US00PP35551P2

(12) United States Plant Patent
Bedford et al.

(10) Patent No.: US PP35,551 P2
(45) Date of Patent: Dec. 19, 2023

(54) PEAR TREE NAMED 'MN121'

(50) Latin Name: ***Pyrus communis* x *pyrifolia***
Varietal Denomination: MN121

(71) Applicant: REGENTS OF THE UNIVERSITY OF MINNESOTA, Minneapolis, MN (US)

(72) Inventors: David S. Bedford, New Germany, MN (US); James J. Luby, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/101,164

(22) Filed: Jan. 25, 2023

Related U.S. Application Data

(63) Continuation of application No. 63/307,719, filed on Feb. 8, 2022.

(51) Int. Cl.
*A01H 5/08* (2018.01)
*A01H 6/74* (2018.01)

(52) U.S. Cl.
USPC ..... Plt./176
CPC ..... *A01H 6/7481* (2018.05)

(58) Field of Classification Search
USPC ..... Plt./176
CPC ..... A01H 5/0881
See application file for complete search history.

*Primary Examiner* — Kent L Bell
(74) *Attorney, Agent, or Firm* — Penny J Aguirre

(57) ABSTRACT

A new cultivar of pear tree named 'MN121' that is characterized by its good cold hardiness in U.S.D.A. Zone 4; observed for 30 years, its lack of fire blight infection in field observations on test trees, its fruit with a storage life of approximately three months in refrigerated storage with ambient atmosphere, its fruit that ripen in mid-August in central Minnesota, its fruit with a crisp texture and a sweet and pleasing flavor similar to that of an Asian pear, its fruit that is oval to elliptic in shape, and its fruit that may be picked ripe for immediate consumption with no after-ripening required.

3 Drawing Sheets

Botanical classification: *Pyrus communis* x *pyrifolia*.
Varietal denomination: 'MN121'.

BACKGROUND OF THE INVENTION

The present invention relates to a new and distinct cultivar of pear tree, botanically known as *Pyrus communis* x *pyrifolia* 'MN121', referred to hereafter by its cultivar name, 'MN121'. 'MN121' is a new cultivar of pear tree for use in commercial pear production and home gardens.

The new cultivar is the result of a controlled breeding program conducted by the inventors at a research center near Victoria, Minnesota. The objective of the breeding program was to develop a new pear cultivar that is cold hardy in U.S.D.A. Zone 4 combined with fruit that has the crisp texture of an Asian pear.

The new pear tree arose from a cross made in 1988 between 'Shinseiki' (not patented) as the female parent and 'Summercrisp' (not patented) as the male parent. The inventors selected 'MN121' as a single unique tree amongst the seedlings from the above cross in 2004 near Victoria, Minnesota.

Asexual propagation of the new cultivar was first accomplished by bud grafting in 2004 under the direction of the inventors near Victoria, Minnesota. Asexual propagation by bud grafting has determined that the characteristics of the new cultivar are stable and are reproduced true to type in successive generations.

SUMMARY OF THE INVENTION

The following traits have been repeatedly observed and represent the characteristics of the new cultivar and distinguish 'MN121' as a unique cultivar of pear tree.

1. 'MN121' exhibits good cold hardiness in U.S.D.A. Zone 4; observed for 30 years.
2. 'MN121' has exhibited no evidence of fire blight infection in field observations on test trees.
3. 'MN121' exhibits fruit with a storage life of approximately three months in refrigerated storage with ambient atmosphere.
4. 'MN121' exhibits fruit that ripen in mid-August in central Minnesota.
5. 'MN121' exhibits fruit with a crisp texture and a sweet and pleasing flavor similar to that of an Asian pear.
6. 'MN121' exhibits fruit that is oval to elliptic in shape.
7. 'MN121' exhibits fruit that may be picked ripe for immediate consumption with no after-ripening required.

The female parent of 'MN121' differs from 'MN121' in having fruit that are more blocky round in shape and trees that do not survive in U.S.D.A. Hardiness Zone 4. The male parent of 'MN121' differs from 'MN121' in having fruit that are more pyriform in shape. 'MN121' can also be compared to the *Pyrus* cultivars 'Gourmet' (not patented) and 'Luscious' (not patented). 'Gourmet' and 'Luscious' are both similar to 'MN121' in being cold hardy in U.S.D.A. Zone 4. 'Gourmet' and 'Luscious' both differ from 'MN121' in having fruit that matures later in the season and requires additional ripening after harvest.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited to website listings by The University of Minnesota.

BRIEF DESCRIPTION OF THE DRAWINGS

The accompanying color photographs were taken of 'MN121' trees 12 years in age that were grown in a trial plot near Victoria, Minnesota.

The photograph in FIG. 1 provides a view of 'MN121' in bloom.

Figure 1:
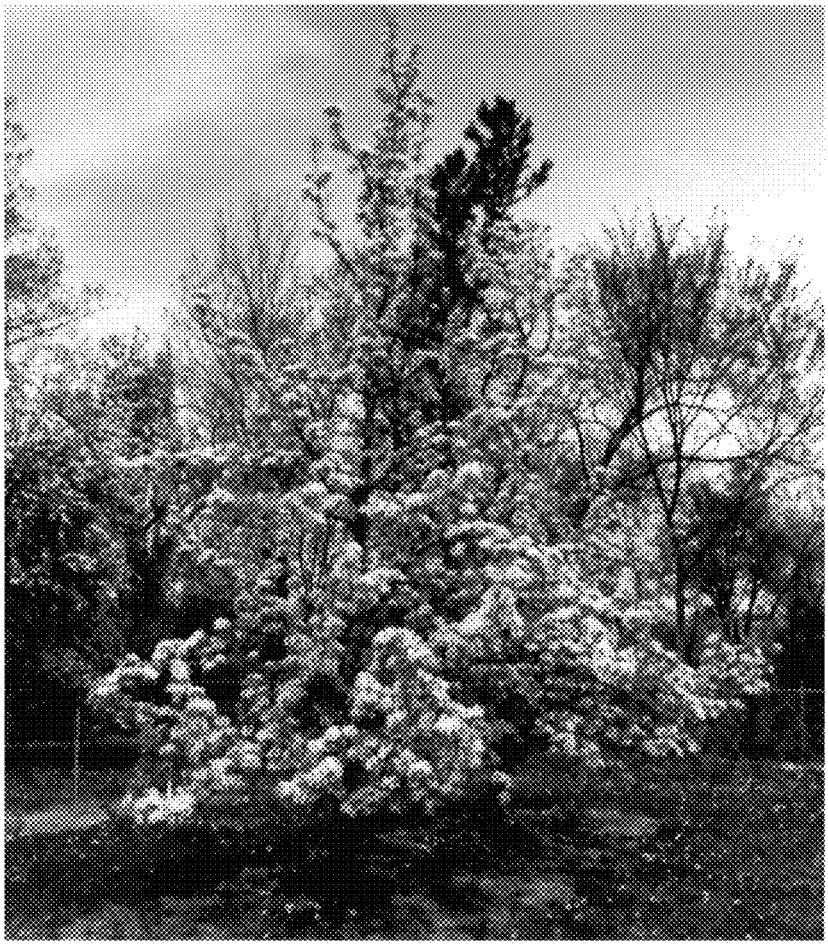
Figure 2:
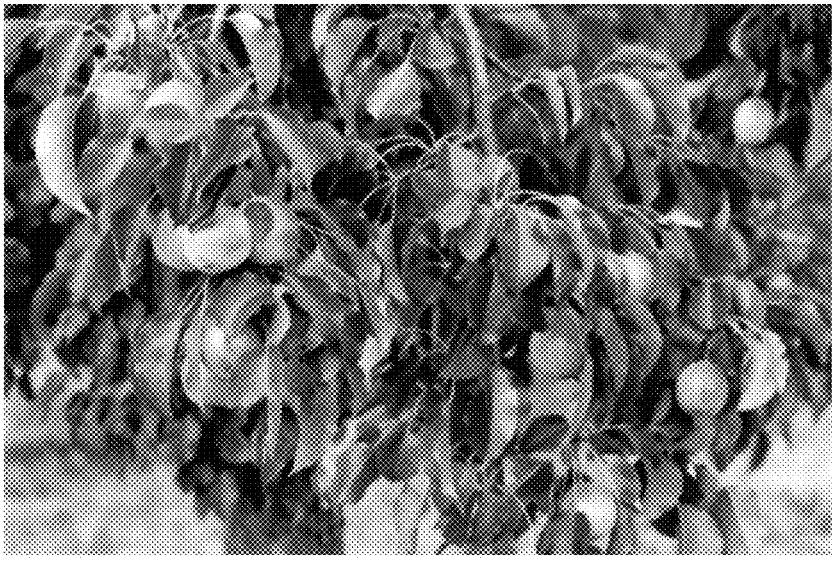

The photograph in FIG. 2 provides a view of the fruit and foliage of 'MN121' on the tree.

Figure 3:
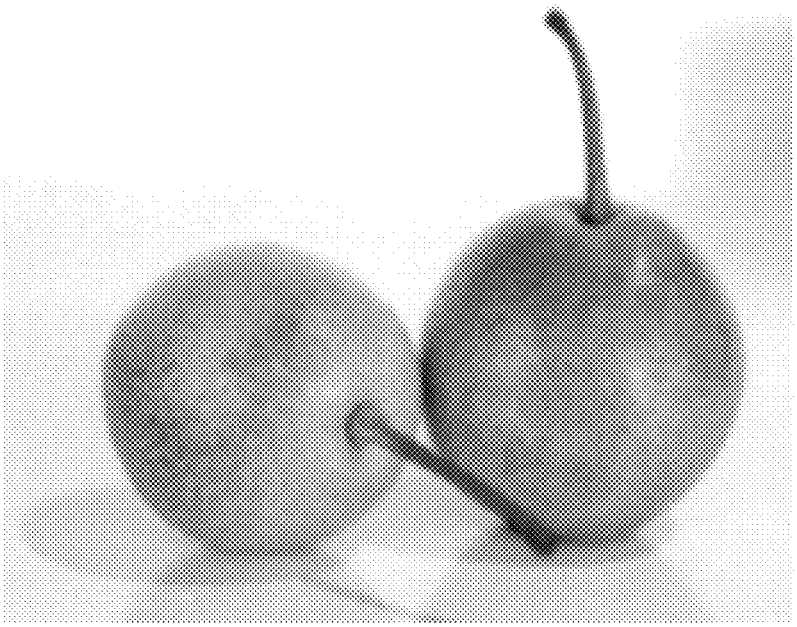

The photograph in FIG. 3 provides a close-up view of the fruit of 'MN121'.

Figure 4:
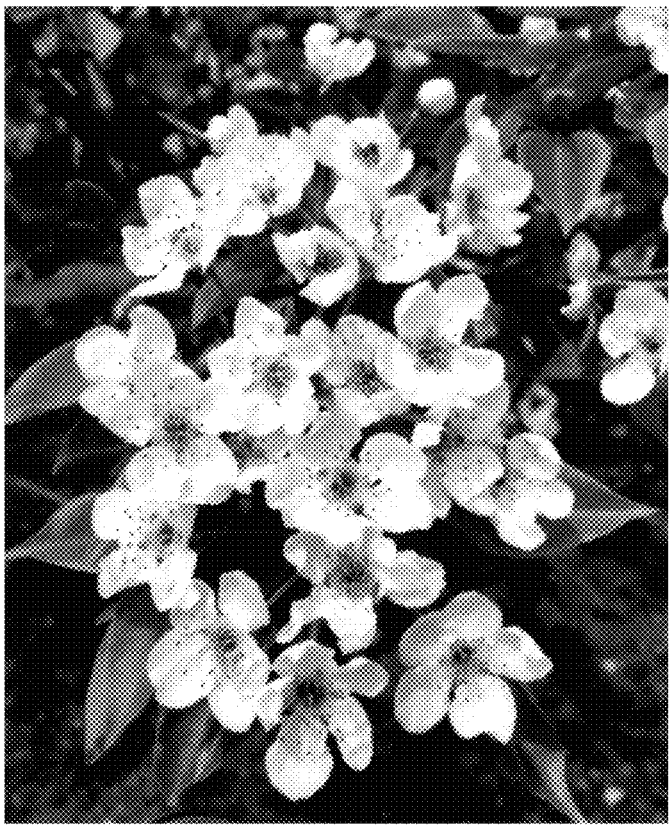

The photograph in FIG. 4 provides a view of the flowers of 'MN121'.

Figure 5:
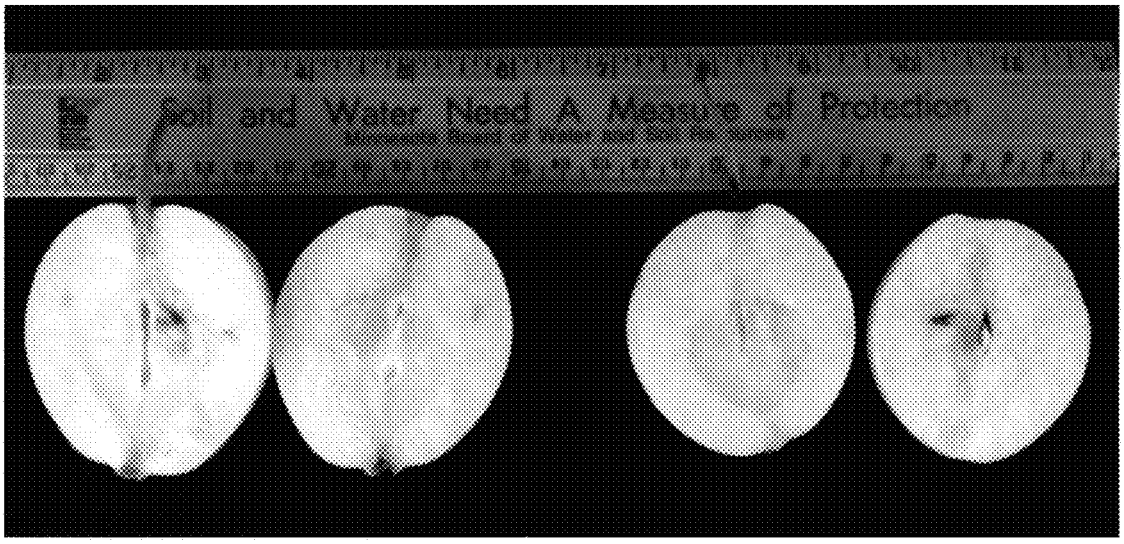

The photograph in FIG. 5 provides a view of the fruit cut longitudinally of 'MN121'.

Figure 6:
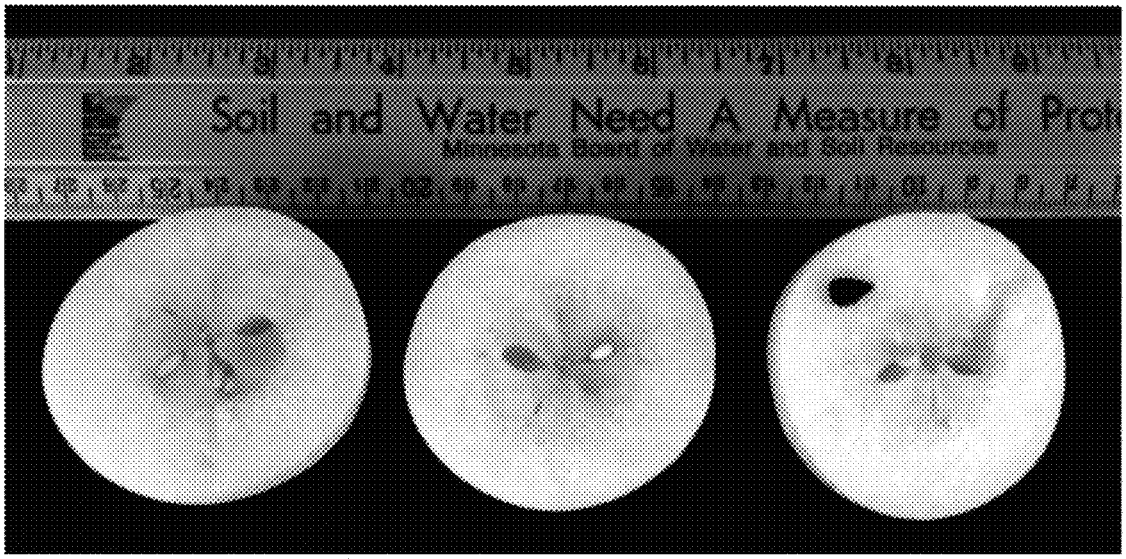

The photograph in FIG. 6 provides a view of the fruit cut horizontally of 'MN121'.

The colors in the photographs are as close as possible with the photographic and printing technology utilized and the color values cited in the detailed botanical description accurately describe the colors of the new pear tree.

DETAILED BOTANICAL DESCRIPTION

The following is a detailed description of the new Pear variety as observed on trees 12 years in age as grown in a trial field near Victoria, Minnesota. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

Tree description:

*Tree habit*.—Upright spreading.

*Tree size*.—An average of 8.5 m in height, 5 m in spread as a 12-year-old tree.

*Growth rate*.—Moderately vigorous.

*Diseases and pests*.—No infection of fire blight (*Erwinia amylovora*) has been observed in field observations to date, no resistance or susceptibility to pests has been observed.

*Cold hardiness*.—At least in U.S.D.A. Zone 4.

*Branching habit*.—Spreading.

*Branch frequency*.—Medium.

*Branch strength*.—Intermediate.

*Branch angle*.—45° to 80°.

*Predominance of bearing*.—Spurs.

*Trunk diameter*.—18 cm at 30 cm above the graft union as a 12 year old tree.

*Branches*.—Lower bearing limbs an average of 8.3 cm in diameter, ranging from 2.6 to 3.3 m in length, lateral branches an average of 3.8 cm in diameter, ranging from 1.8 to 2.3 m in length.

*Trunk color*.—Blend of N199A and N199C.

*Branch surface*.—1 to 2 year old growth smooth, 3 to 5 year old wood becoming rough, 5 year old and older wood exfoliating.

*Trunk texture*.—Young (1 to 2 year); smooth, maturing trunk (3 to 5 years); rough, older wood; exfoliating.

Description of dormant shoots:

*Stem size of one-year-old shoots*.—Average of 36 cm in length, 4.4 mm in diameter.

*Pubescence on upper one-year-old shoot*.—Very sparse, finely puberulent.

*Lenticels on one-year-old shoots*.—Average of 0.5 mm in diameter, round to oblong in shape, approximately 10 lenticels per cm of shoot length, 155B in color.

*Shine of bark*.—Medium.

*Internode length on one-year-old shoots*.—Average of 5 cm.

*Bark color of one-year-old shoots*.—Sun-exposed wood between 183A and 178A, shaded wood between 199B and 152A.

*Three-year-old wood*.—A blend of N200B and N200C in color, surface slightly rough, covered with lenticels 156C in color, 1 to 3 mm in length, 1 mm in width, round to oblong in shape, 15 to 20 per 1.5 sq. cm.

*Angle of three year-old shoot relative to trunk*.—Approximately 45°.

Description of growing shoots:

*Color of growing tip of shoot*.—144B, side facing sun 176B.

*Shape of shoot tip leaves in cross section*.—Concave.

*Pubescence of shoot tip leaves*.—Medium to dense on upper surface and dense on lower surface.

*Distribution of color other than green on shoot tip leaves*.—None.

Leaf description:

*Leaf orientation*.—Outward.

*Leaf division*.—Simple.

*Leaf shape*.—Ovate-elliptic when expanding.

*Leaf size*.—Average of 9.6 cm in length and 6.9 cm in width.

*Leaf apex*.—Acuminate.

*Leaf base*.—Young; rounded, mature; acute.

*Leaf surface*.—Young leaves; before expanding both surfaces are densely covered with short woolly puberulent hairs, expanded leaves are glabrous.

*Leaf aspect*.—Held in an average of 60° from the shoot, blade becoming pendant.

*Leaf margin*.—Serrated.

*Leaf color*.—Young expanding leaves upper surface; 144A, young expanding leaves lower surface; 144B, mature upper surface; 146A to 147A, veins 144C, mature lower surface; 144B, veins 148C.

*Leaf venation*.—Pinnate main veins with netted minor veins.

*Leaf bud*.—Average of 4 mm in length and 3.5 mm in width, satiny and flaky surface, 183B in color.

*Petiole*.—Average of 4 cm in length and 2 mm in diameter, 144B in color, surface densely covered with lanate pubescence matching leaf surface color, held in an average angle of 60° , blade becoming pendulant.

*Stipules*.—Absent.

Flower description:

*Beginning flowering date*.—Typically from May 1st to May 10th near Victoria, Minnesota.

*Number of flowers*.—Typically 8 per spur.

*Inflorescence type*.—Cluster, corymb-like, extended base.

*Inflorescence size*.—An average of 9.3 cm in diameter and 6.3 cm in depth.

*Flower buds*.—Globose in shape, an average of 1.3 cm in length and diameter, color; 155A with sepal portion N155B with N155A at tips, surface is glabrous with sepal portion pubescent.

*Flower size*.—Average of 3.3 cm in diameter and 1.4 cm in depth.

*Flower fragrance*.—Highly fragrant, vegetal.

*Flower aspect*.—Upright to outward facing.

*Petals*.—5, sometimes 6 per flower, un-fused, lower ½ to ⅓ overlapping, broad ovate, concave in shape, flat to rounded apex, margins entire, with one or two notches at the apex, base flat aspect 2 mm attachment to sepal, an average of 1.7 cm in length and 1.6 cm in width at widest point and 1.2 mm in width at narrowest point, both surfaces glabrous and satiny, color; upper and lower surface color when opening and fully open 155A.

*Sepals*.—5, free lobes; lanceolate, reflexed in shape, entire margin, acuminate apex, based fused into a cup-like base, lobes an average of 5.7 mm in length and 2.7 mm in width (at base), both surfaces smooth and covered with sparsely, finely puberulent, <1 mm in length, color; N144A on outer surface, 152B on inner surface when flowering is opening.

*Pedicel*.—Average of 3.8 cm in length and 1.5 mm in width, held upright to outward, moderately strong, surface densely covered with woolly matted puberulent hairs <0.5 mm in length, color; N144D, base N144A.

*Bracts*.—None.

*Pistil*.—1, with 5 styles, 1.1 cm in length, style; 5 mm in length and 0.5 mm in width, 144B in color, stigma; angled and rounded, 152C in color, ovary; 4 mm in length and 2.5 mm in width, 144C in color.

*Stamens*.—Average of 24, anther; bi-fid, slightly curved, 0.5 mm in width, 1 mm in length, color; 63B before dehiscence, N187A after dehiscence, pollen; moderate in quantity, 4C in color, filament; 6 mm in length and 0.3 mm in width, 144D in color, nectar; copious amounts at the base of stamens.

*Pollination requirements*.—Low self-compatibility, production is moderate, fertile as male in hand pollinations, fertile as female in hand pollinations.

Fruit description:

*Fruit size*.—Medium, average of 5 cm in diameter and 5.2 cm in length.

*Position of maximum diameter*.—At midpoint between proximal and distal ends.

*Fruit shape*.—Oval to elliptic.

*Fruit symmetry*.—Slightly asymmetrical.

*Fruit prominence of ribbing*.—Absent.

*Size of eye (calyx)*.—Aperture 5.9 mm, width 11.3 mm, height 2.4 mm.

*Persistence of calyx*.—Present.

*Length of sepal*.—3.6 mm.

*Spacing of sepals at base*.—Touching.

*Depth of eye basin*.—Shallow 1 to 2 mm.

*Width of eye basin*.—Ranges from 13 to 20 mm, Average of 16 mm.

*Thickness of stalk*.—Medium.

*Stalk color*.—151A and 166A and 166B as the stalk ages and dries.

*Stalk size*.—3 mm in diameter, 4.2 cm in length.

*Depth of stalk cavity*.—Ranges from 2 to 4 mm, mean 2.9 mm.

*Width of stalk cavity*.—Ranges from 14 to 20 mm, mean of 1.46 cm.

*Relief of surface*.—Smooth.

*Bloom of skin*.—None to slight.

*Waxiness of skin*.—Slight.

*Thickness of skin*.—Medium.

*Skin color*.—Ground color; 14C when ripe, overcolor 34A; area ranges from 1 to 30% depending on sun exposure of fruit on the tree.

*Presence of russet*.—Low, positioned around the stalk cavity and lenticels.

*Lenticels*.—Medium (average of 1 mm).

*Color of flesh*.—155A.

*Distinctness of core line*.—Medium to strong, partially surrounded by stone cells.

*Aperture of locules*.—Open.

*Fruit set*.—Medium to high.

*Fruit per cluster*.—1 to 3.

*Fruit maturity date*.—August 15 to 25 near Victoria, Minnesota.

*Seed*.—202A in color, deltoid in shape, an average of 8.7 mm in length and 5 mm in diameter, an average of 8.7 seeds/fruit.

*Browning of flesh*.—Weak to medium.

*Firmness (without skin)*.—Moderately firm, average of 14.6 pounds at harvest using a hand-held Effigi fruit pressure tester with an 11 mm tip.

*Texture of flesh*.—Crisp.

*Cropping frequency*.—Annual.

*Fruit flavor*.—Sweet with mild tropical fruit flavors.

*Fruit weight*.—Average of 79 g.

*Fruit productivity*.—Moderate; an average of 40 lbs/tree per season (15-year-old tree).

*Juiciness*.—Medium.

*Acidity*.—Low.

*Soluble solids content*.—Average of 13.1° Brix at harvest.

*Storage life*.—Approximately 111 days in ambient atmosphere storage (average temperature of 34° F.); observed for 11 years.

*Market use*.—Fresh Fruit.

It is claimed:

1. A new and distinct variety of pear tree named 'MN121' as herein illustrated and described.

* * * * *